(12) United States Patent
Orton

(10) Patent No.: US 6,181,962 B1
(45) Date of Patent: *Jan. 30, 2001

(54) ELECTRICALLY ACTIVATED SUBSTANCE AND METHOD FOR MAKING THE SAME

(76) Inventor: Kevin R. Orton, 257-G Avenida Lobeiro, San Clemente, CA (US) 92672

(*) Notice: Under 35 U.S.C. 154(b), the term of this patent shall be extended for 0 days.

This patent is subject to a terminal disclaimer.

(21) Appl. No.: 09/259,120

(22) Filed: Feb. 26, 1999

Related U.S. Application Data

(63) Continuation of application No. 08/865,253, filed on May 29, 1997, now Pat. No. 5,885,241.

(51) Int. Cl.[7] ............................................. A61N 1/30
(52) U.S. Cl. ................................................. 604/20
(58) Field of Search ................................... 604/20

(56) References Cited

U.S. PATENT DOCUMENTS

| | | |
|---|---|---|
| 397,474 | 2/1889 | Stanley . |
| 408,607 | 8/1889 | Flint . |
| 882,378 | 3/1908 | Friendlich . |
| 1,108,686 | 8/1914 | Bonis . |
| 3,163,166 | 12/1964 | Brant et al. . |
| 3,794,022 | 2/1974 | Nawracaj . |
| 4,180,079 | 12/1979 | Wing . |
| 4,407,282 | 10/1983 | Swartz . |
| 4,446,870 | 5/1984 | Wing . |
| 4,572,194 | 2/1986 | Head . |
| 4,602,909 | 7/1986 | Csilik et al. . |
| 4,926,881 | 5/1990 | Ichinomiya et al. . |
| 4,942,884 | 7/1990 | Ichinomiya et al. . |
| 4,944,302 | 7/1990 | Hernandez et al. . |
| 4,980,038 | 12/1990 | Watanabe et al. . |
| 5,012,816 | 5/1991 | Lederer . |
| 5,058,605 | 10/1991 | Slovak . |
| 5,188,738 | 2/1993 | Kaali et al. . |
| 5,350,415 | 9/1994 | Cywinski . |
| 5,885,241 | * 3/1999 | Orton ........................... 604/20 |

FOREIGN PATENT DOCUMENTS

| | | |
|---|---|---|
| 0 377 057 | 7/1990 | (EP) . |
| 2 621 827 | 4/1989 | (FR) . |
| WO 96 06656 | 7/1996 | (WO) . |

OTHER PUBLICATIONS

Web Page–www.angelfire.com/biz/Korean Waterlonizer/index.html "Korean Water Ionizer" 2 pgs.
Web Page–www.alternativemedicine.com/digest/issue09/i09–a25.shtml "Rejuvenation Keys" 2 pgs.
Email Advertisemet—Introducing: Microwater Series On, Presented by High Tech $H_2O$. 5 pgs.
Email Adertisement—"THM Microwater ' The Microwater Unit" 2 pgs.

* cited by examiner

Primary Examiner—William E. Kamm
(74) Attorney, Agent, or Firm—Knobbe, Martens, Olson & Bear LLP

(57) ABSTRACT

An electrically active substance is prepared by flowing a high frequency alternating electric current through an electrolytic material, such as distilled water with NaCl dissolved therein, so as to change a physical property of the material. The alternating current is caused to flow through the electrolytic substance for preferably 4 to 8 hours. The current flow is then removed and the resulting electrically activated substance is then applied to human or animal skin to provide cosmetic/medical benefits, such as the reduction of skin wrinkles, preferably within 4 days. The substance may also be orally ingested.

46 Claims, 7 Drawing Sheets

ELECTRICALLY ACTIVATED SUBSTANCE AND METHOD FOR MAKING THE SAME

This application is a continuation of U.S. application Ser. No. 08/865,253, filed May 29, 1997, now U.S. Pat. No. 5,885,241, and issued Mar. 23, 1999.

FIELD OF THE INVENTION

The present invention relates generally to cosmetic/medical therapy and more particularly to an electrically activated substance for use in such therapy.

BACKGROUND OF THE INVENTION

The use of transcutaneous electrotherapy to treat cosmetic/medical conditions is well known. Transcutaneous electrotherapy involves the passage of an electrical current from one electrode to another, such that the therapeutic current is caused to pass directly through a target tissue of the patient. Exemplary devices used in the performance of transcutaneous electrotherapy are provided in U.S. Pat. Nos. 397,474; 3,794,022; 4,180,079; 4,446,870; 5,058,605; in French Patent 2621-827-A; and European Patent Application EP-377-057-A.

Although the use of transcutaneous electrotherapy has proven beneficial, such contemporary cosmetic/medical therapy suffers from inherent disadvantages. For example, during transcutaneous electrotherapy electrical current passes through the target tissue of the patient. Many patients may find this painful or otherwise undesirable. Further, transcutaneous electrotherapy is generally not self-administrable, and therefore generally requires the presence of a skilled operator. The administration of transcutaneous electrotherapy also tends to be costly.

In view of the foregoing, it is desirable to provide an effective alternative to transcutaneous electrotherapy wherein electric current is not caused to flow through the treated tissue of the patient, which is self-administrable and which is comparatively inexpensive.

SUMMARY OF THE INVENTION

The present invention specifically addresses and alleviates the above-mentioned deficiencies associated with the prior art. More particularly, the present invention comprises a method for providing cosmetic/medical therapy, the method comprising the steps of electrically activating a substance and administering the electrically activated substance to a subject. Administering the electrically activated substance to the subject provides a cosmetic/medical benefit to the subject.

Although, the subject as described herein, is a human being, those skilled in the art will appreciate that the methodology of the present invention may be practiced upon various different animals. Thus, the use of a human being in this application is by way of example only and not by way of limitation.

The electrically activated substance is applied topically to treat skin problems such as wrinkles, cuts, abrasions, etc. The electrically activated substance may also be ingested, so as to treat internal medical conditions, where indicated.

According to the preferred embodiment of the present invention, the electrically activated substance comprises water, preferably distilled water. However, as those skilled in the art will appreciate, various other substances, particularly those comprised of simple molecules, may likewise be utilized.

The step of electrically activating the substance comprises applying an electrical signal to the substance. According to the preferred embodiment of the present invention, an alternating current signal, preferably having a generally symmetric waveform, is utilized. Thus, for example, a sinusoidal waveform, a square waveform, and a triangular waveform are suitable. Those skilled in the art will appreciate that various other generally symmetric waveforms are likewise suitable.

The electrical signal preferably comprises an alternating current signal having a frequency of between approximately 5 or 10 KHz and approximately 1 MHz, preferably between approximately 50 KHz and approximately 100 KHz. According to the preferred embodiment of the present invention, the frequency of the electrical signal is varied within a frequency range of approximately 50 KHz to 100 KHz.

Preferably, the alternating current has approximately zero direct current bias. In order to mitigate direct current bias, the electrical signal is preferably applied to the substance via a capacitor-resistor network. Alternatively, the electrical signal is applied to the substance via an isolation transformer.

The electrical signal preferably has a voltage of between approximately 50 volts rms and approximately 150 volts rms.

The electrical signal is applied to the substance to be electrically activated via at least one pair of electrodes. As those skilled in the art will appreciate, a plurality of pairs of electrodes may be utilized, if desired. The electrodes are preferably comprised of either a biologically inert, non-reactive metal or a non-metallic material having a low atomic number. For example, it has been found that gold, carbon 12, and graphite-carbon loaded thermo-plastic material are suitable.

When distilled water is to be electrically activated, then a substance is added to the water to form an electrolyte therefrom, so as to facilitate current flow therethrough. According to the preferred embodiment of the present invention, sodium chloride (table salt) is utilized to form an electrolyte from distilled water.

It has also been found that tap water is typically suitable and does not generally require the addition of any other substance thereto.

According to the preferred embodiment of the present invention, the substance, e.g., sodium chloride, is added to the distilled water while monitoring current flow therethrough, until the desired current is obtained.

According to a preferred embodiment of the present invention, approximately 1 amp rms of current is caused to flow through the substance being electrically activated. Typically, a voltage of approximately 100 volts rms is required to effect a current of 1 amp rms. It has been found that currents as low as 1 milliamp may be used, if desired. Preferably, at least 10 milliwatts of power per milliliter of substance as utilized. Those skilled in the art will appreciate that the voltage required to effect the desired current is dependant upon the conductivity of the substance being electrically activated. The electrodes preferably have a resistance below 500 ohms per square centimeter, preferably below 50 ohms per square centimeter.

When administered topically, approximately 0.05 ml of the electrically activated substance is applied per square centimeter of treatment area. The electrically activated substance is preferably administered 3 to 6 times with approximately 1 to 4 days between administrations.

Such topical application of the electrically activated substance of the present invention has been found to be effective in mitigating wrinkles on human skin.

When taken orally, approximately 2 ml of the electrically activated substance is preferably ingested per day for approximately 6 weeks.

These, as well as other advantages of the present invention will be more apparent from the following description and drawings. It is understood that changes in the specific structure shown described may be made within the scope of the claims without departing from the spirit of the invention.

DETAILED DESCRIPTION OF THE PREFERRED EMBODIMENT

The detailed description set forth below in connection with the appended drawings is intended as description of the presently preferred embodiment of the invention and is not intended to represent the only form in which the present invention may be constructed or utilized. The description sets forth the functions and the sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

The electrically activated substance and method for making the same of the present invention are illustrated in FIGS. 1–4 of the drawings which depict a presently preferred embodiment thereof.

Figure 1:
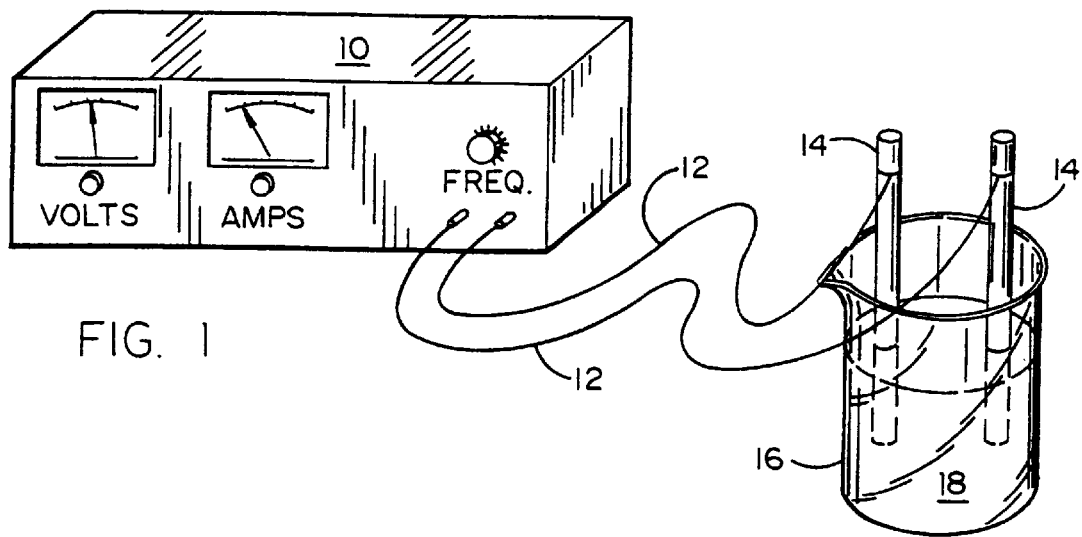
FIG. 1 is a perspective view showing a variable frequency current source being utilized to electrically charge a liquid contained within a beaker.

Referring now to FIG. 1, according to the present invention a variable frequency current source 10 is electrically connected, via wires 12 to probes or electrodes 14 which are at least partially immersed within the substance 18 to be electrically activated, which is contained within beaker 16.

The variable frequency current source 10 preferably comprises the variable frequency current source having an output frequency range from approximately 10 KHz to approximately 1 MHz, having a voltage output from approximately 50 volts rms to 150 volts rms, and having a maximum current output in excess of 1 amp rms.

According to the preferred embodiment of the present invention, the variable frequency current source 10 provides an alternating current output having substantially 0 direct current bias.

The variable frequency current source 10 is capable of providing a generally symmetric waveform, such as a sinusoidal waveform, a square waveform, and/or a triangular waveform. As those skilled in the art will appreciate, various other generally symmetrical alternating current waveforms are likewise suitable.

According to the preferred embodiment of the present invention, the frequency output of the variable frequency current source 10 is capable of being swept or automatically varied between a minimum and maximum frequency. Alternatively, the variable frequency current source 10 is capable of being manually swept in frequency.

The wires 12 preferably comprise copper wires having a current rating sufficient to carry the required current, e.g., 1 amp rms, without excessive heating.

Each electrode 14 is preferably comprised of a chemically and biologically inert material, preferably a non-reactive metal such as gold, or alternatively, a non-metal having a low atomic number. It is believed that it is not desirable to have ions form from the substance of the electrodes. For example, if lead electrodes are utilized, it has been found that lead ions permeate the substance being electrically activated, potentially resulting in undesirable contamination of the medium and potential poisoning of the patient to whom the electrically activated substance is administered. Although aluminum and copper electrodes may be suitable in some applications, they are generally thought to be undesirable.

Carbon 12 has been found to be suitable for the construction of electrodes according to the present invention. More particularly, carbon electrodes may be formed utilizing contemporary plastic injection molding techniques wherein a graphite-carbon loaded thermo-plastic material, such as nylon, is injected into the molds.

Typical dimensions for the electrodes 14 are 3 mm thick, 20 mm wide, and 10 cm long. However, as those skilled in the art will appreciate, various different dimensions and cross-sectional configurations, e.g., round, oval, square, triangular, etc., may likewise be suitable. According to the preferred embodiment of the present invention, the electrical resistance of the finished electrodes is preferably less than 500 ohms/cm$^2$, preferably less than 50 ohms/cm$^2$.

Further, according to the preferred embodiment of the present invention, the two electrodes are positioned several centimeters apart in a 250 ml container, e.g., a beaker. The container is formed of a non-metallic material, such as glass. Thus, as described herein, the method for electrically activating a substance is preferably practiced utilizing approximately 200 ml of the substance at a time. Those skilled in the art will appreciate that the quantity of substance electrically activated may be varied by varying the dimensions of the container, electrodes, and by varying the strength of the electrical signal appropriately.

Preferably, current flow through the substance 18 being electrically activated is monitored as an electrolytic substance is added thereto so as to form an electrolyte. For example, when water is being electrically activated, then sodium chloride is added to the water, so as to form an electrolyte. As the sodium chloride is added to the water, current flow through the water is monitored until the desired current flow is achieved, thereby indicating that sufficient sodium chloride has been added to the water.

According to the preferred embodiment of the present invention, approximately 1 amp rms of current is caused to flow through the substance being electrically activated while a voltage of approximately 100 volts rms is applied thereto. Those skilled in the art will appreciate that various different voltage and amperage levels are likewise suitable.

Typically, current is caused to flow through the substance being electrically activated 18 until small gas bubbles are formed upon the electrodes. This typically takes approximately 4 to 8 hours. When small gas bubbles are observed on the electrodes, then the substance has been fully electrically activated and is ready to use.

The degree to which the substance is electrically activated, and thus the effectiveness thereof in cosmetic/medical therapy, is directly related to the voltage applied to the electrodes, the spacing of the electrodes, the current caused to flow between the electrodes, and, to some extent, the length of time that the current is applied. Current must be caused to flow between the electrodes for a minimum of at least 10 minutes before any usable results are typically obtained. It is thought that the application of current for a time period in excess of 8 hours produces little additional effectiveness of the electrically activated substance.

The electrically activated substance is typically active for only a limited amount of time after current flow therethrough has ceased. The electrically activated substance is thought to be most effective if utilized within approximately 4 hours after its production. The electrically activated substance is thought to be somewhat effective for up to 4 days after its production. It is believed that the decay in the effectiveness of the electrically activated substance is logarithmic in nature, with more than half of the effectiveness thereof lost within approximately 24 hours.

The specified values for the applied voltage, duration, and conductivity of the medium may be varied, as desired. Indeed, a reduction in the effectiveness of the electrically activated substance may be compensated for by varying one or the other of the production parameters.

A lower voltage may be utilized if additional sodium chloride is added to the solution. However, if too much sodium chloride is added, then the solution may become less bio-compatible. Conversely, if less sodium chloride is utilized, then a higher voltage is necessary to obtain sufficient current flow through the substance. Inadequate current flow through the substance results in substantially reduced effectiveness of the electrically activated substance.

It is thought that the electrically activated substance of the present invention provides beneficial cosmetic/medical effects by stimulating the well known current of injury commonly associated with tissue trauma. As those skilled in the art will appreciate, when tissue is injured, a small electric current is generated. This current is a result of a voltage producing charge imbalance which occurs when portions of previously connected tissue are disconnected from one another, such as occurs if a bone is broken or skin is torn. This voltage causes a small amount of current, e.g., electrons or ions, to flow from one point to another within the tissue. Further disclosure of this effect can be found in *The Body Electric*, by Robert Becker, M.D., among others.

The tissue disconnection of an injury thus upsets the electrical balance of the biological circuit, thereby resulting in the production of a very small current, typically on the order of nanoamps or less. The presence of this electric current is instrumental in the formation of blastema, which are a collection of primitive, unformed cells, which gather at an entry site and later developed into replacement tissue.

It is thought that the electrically activated substance of the present invention effects in biological tissue a disruptive electrical imbalance, similar to that which occurs when a mechanical strain to the tissue has occurred. This electrical imbalance then triggers accelerated metabolic activity in the treatment area. Blood flow accelerates while cellular metabolic activity and interactions increase. Capillaries dilate and there is increased activity toward restored homeostasis. In this process, toxins, free radicals, metabolic waste products, and unused remnant material may be re-formed or flushed away.

It is thought that the electrically activated substance of the present invention should not be applied to fresh injury sites, since it may interfere with the timing and development of the natural current of injury, thereby inhibiting the healing process. However, once the injury has stabilized, the electrically activated substance of the present invention may be applied thereto so as to enhance or re-activate the healing process.

One exemplary use of the electrically activated substance of the present invention is the removal of skin wrinkles. For example, facial wrinkles may be treated with electrically activated water. Preferably, the water is activated with a frequency of between approximately 50 KHz and 100 KHz. It has been found that such electrically activated water is particularly beneficial to the skin and other soft tissue. Such electrically activated water is preferably spritzed or dabbed onto the skin for topical application thereto. The typical dose rate is approximately 0.05 ml/cm$_2$ of treatment area. Mitigation of skin wrinkles typically occurs beginning within approximately 30 minutes, with the results being clearly visible.

Blood flow and metabolic activity accelerates and has been found to peak within approximately 45 minutes after the application of the electrically activated substance of the present invention. After this period of increased blood flow and accelerated metabolism, the skin and tissue enters a recovery phase wherein the cellular structure thereof is rebuilt. Skin begins to draw together, getting tighter, thicker, and causing wrinkles to shrink. Additional collagen forms at the site of treatment.

This recovery phase typically has a duration of approximately 1 to 4 days. After 4 days, approximately all such recovery has occurred. At the end of the recovery phase, another treatment may be applied. It has been found that the recovery phase must be complete before a subsequent treatment, so as to avoid overwhelming the response mechanism.

It is believed that the improvements obtained via the use of the present invention are essentially permanent in nature. That is, it is believed that new wrinkles will take almost as long to form as the original ones did.

It has been found that approximately 6 such treatment sessions are typically required for the removal of wrinkles. After the first treatment session, at least some, occasionally most or all of the fine line facial wrinkles of 1 mm or less in size are either reduced in size or eliminated altogether. After 3 to 4 treatment sessions, wrinkles of up to 4 mm in size are typically substantially reduced. After approximately 6 treatment sessions, many, if not most or all of the facial wrinkles, including large wrinkles of the forehead are typically substantially eliminated. Typically, 6 treatment sessions, at one session per week for 6 weeks, are utilized. The more degenerated the skin, the more dramatic the results are. Acne is frequently cleared in the process due to increased blood flow. Thus, the general result is renewed skin or tissue, without surgery, grafting, patchwork, dermabrasion, laser vaporization, or other invasive or mechanical techniques.

As a result of such treatments, enhanced elastin and collagen support is provided and typical age sagging is reduced due to the shrinking of the skin by as much as ten to twenty percent.

It has also been found that therapeutic medical benefits may be obtained if the medium is ingested. When taken orally, the dose rate is preferably comparatively small, approximately 2 ml per day for 6 weeks. It is thought that such therapy is particularly beneficial for heart and circulatory problems.

To further appreciate the unique advantages of this process, consider that this technique has been also found at least partially effective in the conversion of surgical scar tissue from a typically necrid white fibrous collagen material back into normal healthy pink skin with nerve sensitivity, blood vessels, and even hair follicles. These results may be obtained with administration of a daily to semi-daily topical application, typically over a 6 month period. As the collagen is initially resistant to absorbing the medium, a vasodilator additive is effective in speeding results by increasing penetration of the medium.

Because the electrically activated substance of the resent invention functions as a transfer agent or medium, at no time is there any current flow from the variable frequency current source through biological tissue. Thus, there is no chance of burns, thereby enhancing the safety of such treatment. Further, there is no muscle contraction or nerve impulse firing as a result of using the electrically activated substance of the present invention, as is common during contemporary transcutaneous electrotherapy.

Figure 2:
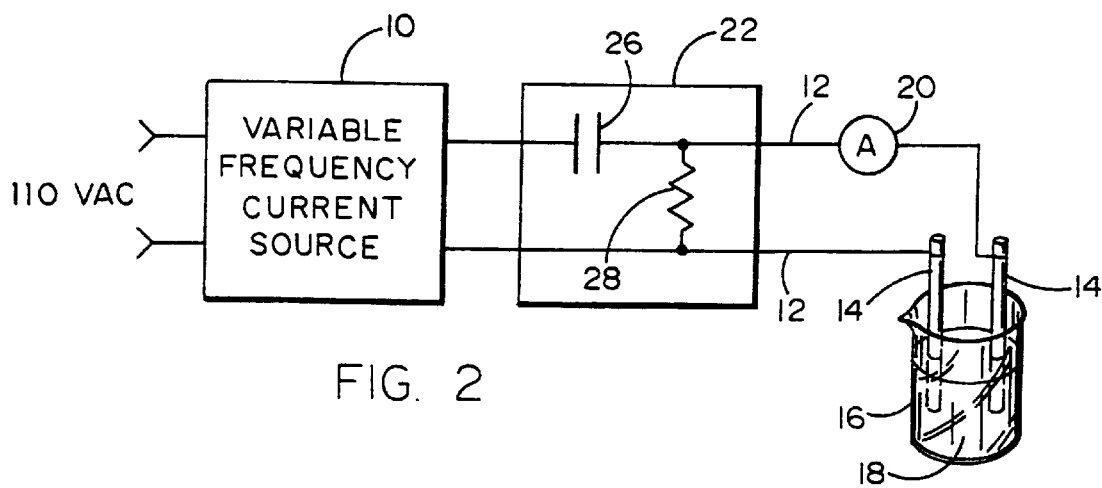
FIG. 2 is a block diagram showing a first alternative configuration of the apparatus of FIG. 1.
Figure 3:
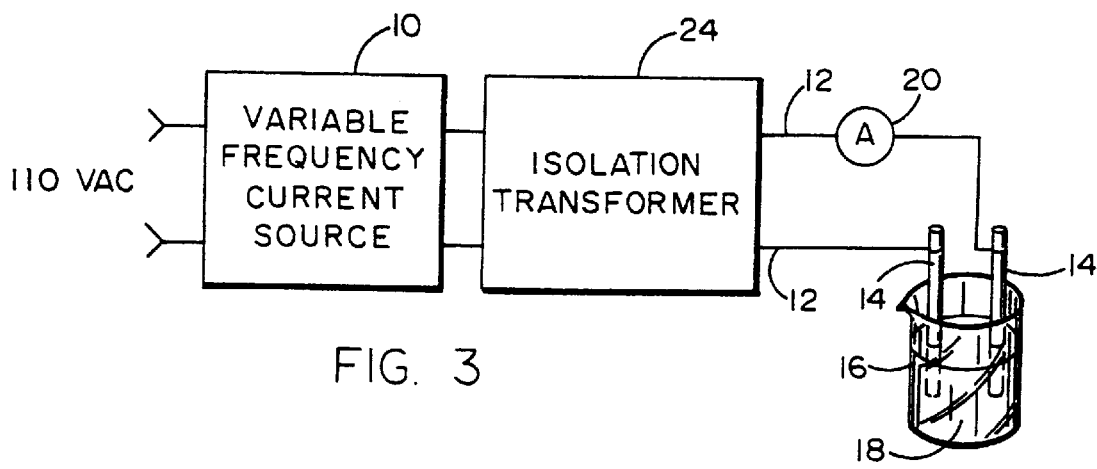
FIG. 3 is a block diagram showing a second alternative configuration of the apparatus of FIG. 1.

Referring now to FIGS. 2 and 3, if the variable frequency current source 10 does not provide approximately 0 direct current bias, then the output thereof can be processed so as to mitigate direct current bias.

With particular reference to FIG. 2, a resistor-capacitor network 22 filters the output of the variable frequency current source 10, so as to mitigate direct current bias. Such a resistor-capacitor network comprises at least one capacitor in series with the substance being electrically activated and at least one resistor in parallel therewith. The resistor-capacitor network 22 functions according to well known principles to mitigate the presence of DC bias in the substance being electrically charged. Those skilled in the art will appreciate that various other types of filters may be utilized. For example, a capacitor inductor network may be utilized.

With particular reference to FIG. 3, an isolation transformer 24 isolates the substance 18 to be electrically charged from direct current bias present in the output of the variable frequency current source 10.

In any instance, when the variable frequency current source 10 does not include a means for monitoring current flow through the substance 18 being electrically activated, then such means is preferably included in the electrical path of the electrodes 14. For example, an amp meter 20 may be inserted in line or applied inductively to one of the wires 12 which provide an electrical pathway for the current which travels between the electrodes 14. Alternatively, an oscilloscope may be utilized to monitor current flow between the electrodes 14.

Figure 4:
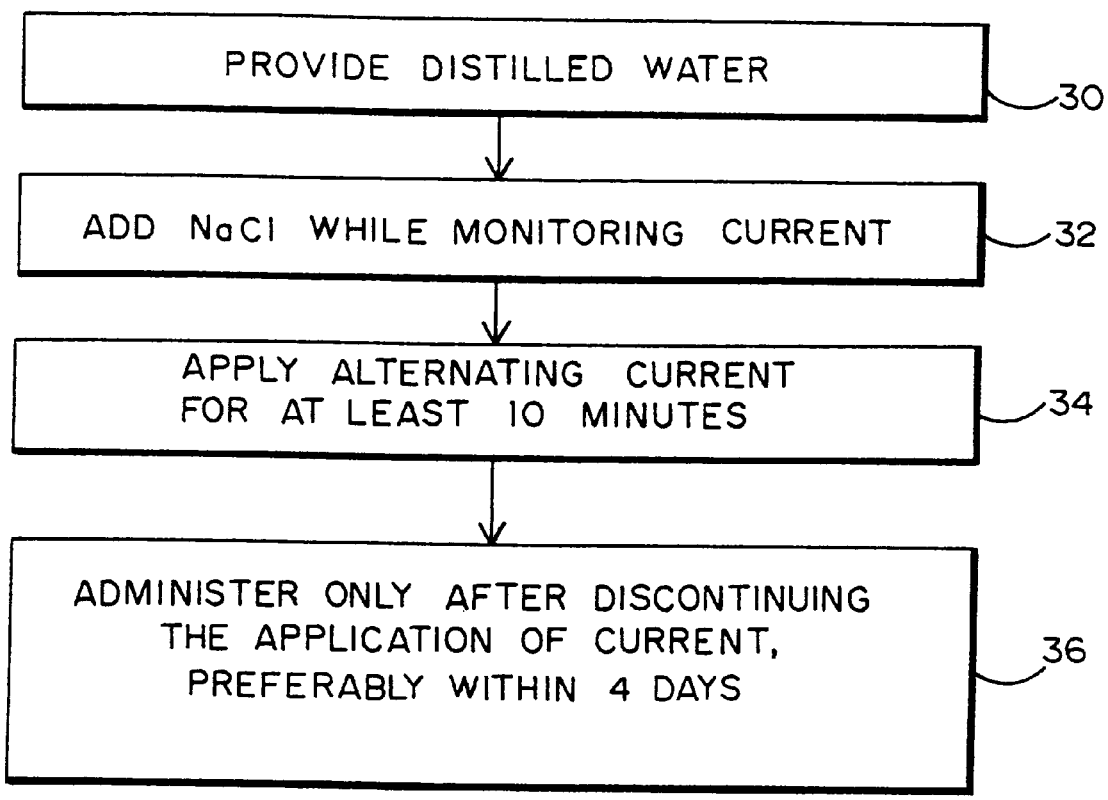
FIG. 4 is a flow chart showing the steps involved in the practice of the method for forming an electrically charged substance, according to the present invention.
Figure 5:
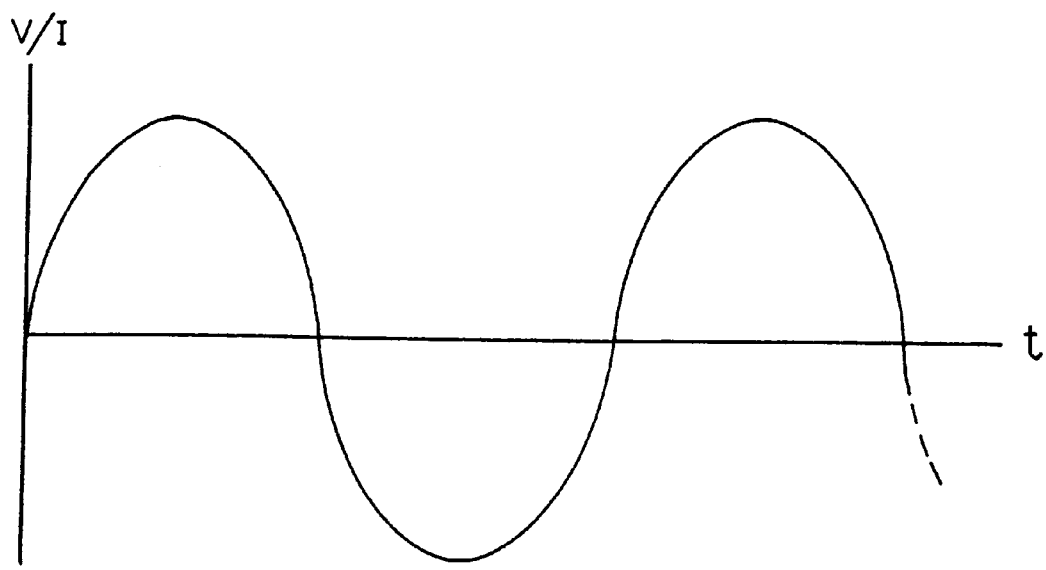
FIG. 5 illustrates a sinusoidal waveform that is generated by the variable frequency current source of FIG. 1 for electrically activating the liquid within the breaker.
Figure 6A:
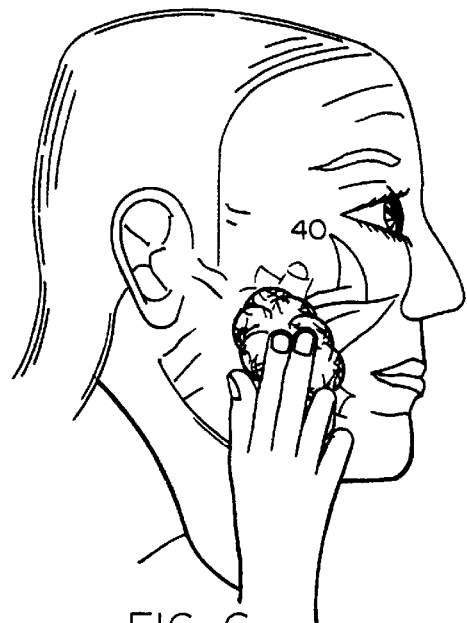
FIGS. 6a and 6b illustrate a recipient before and after receiving a topical application of the electrically charged substance to treat facial wrinkles.
Figure 6B:
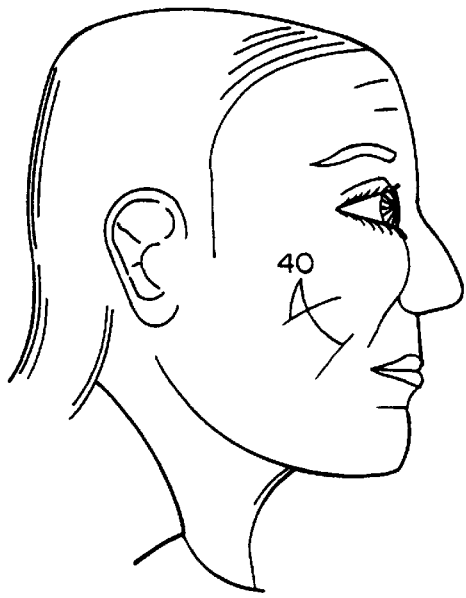
Figure 7A:
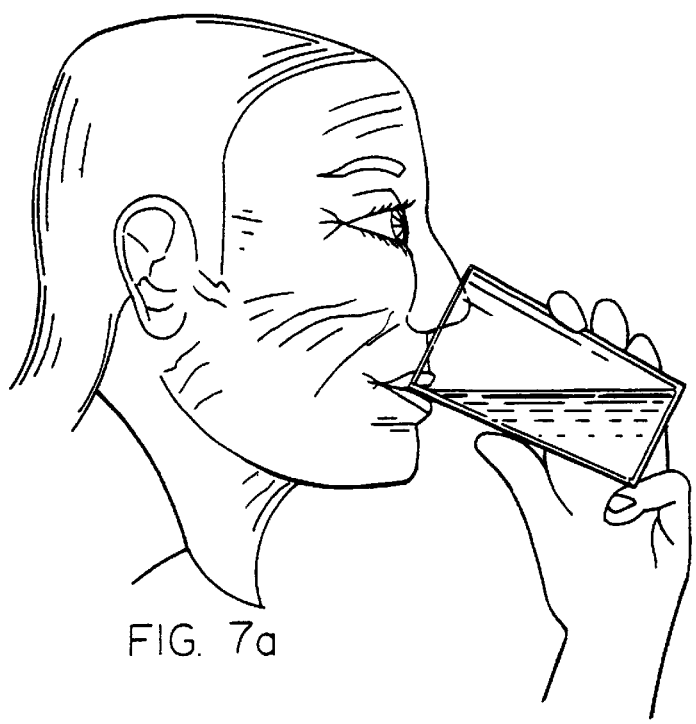
FIGS. 7a and 7b illustrate a recipient before and after ingesting the electrically charged substance to treat facial wrinkles.
Figure 7B:
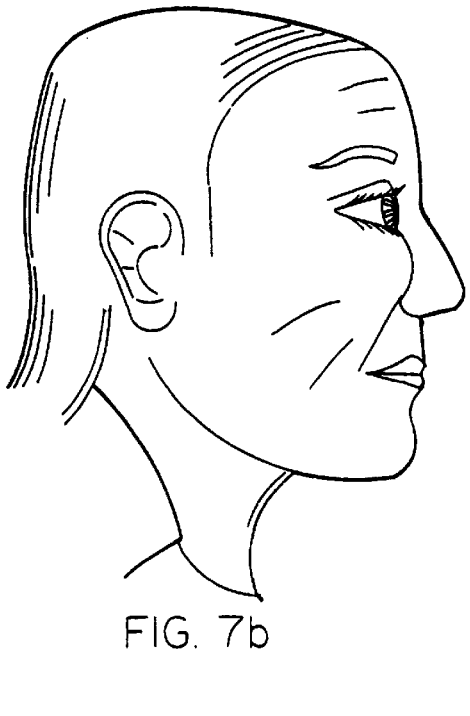
Figure 8A:
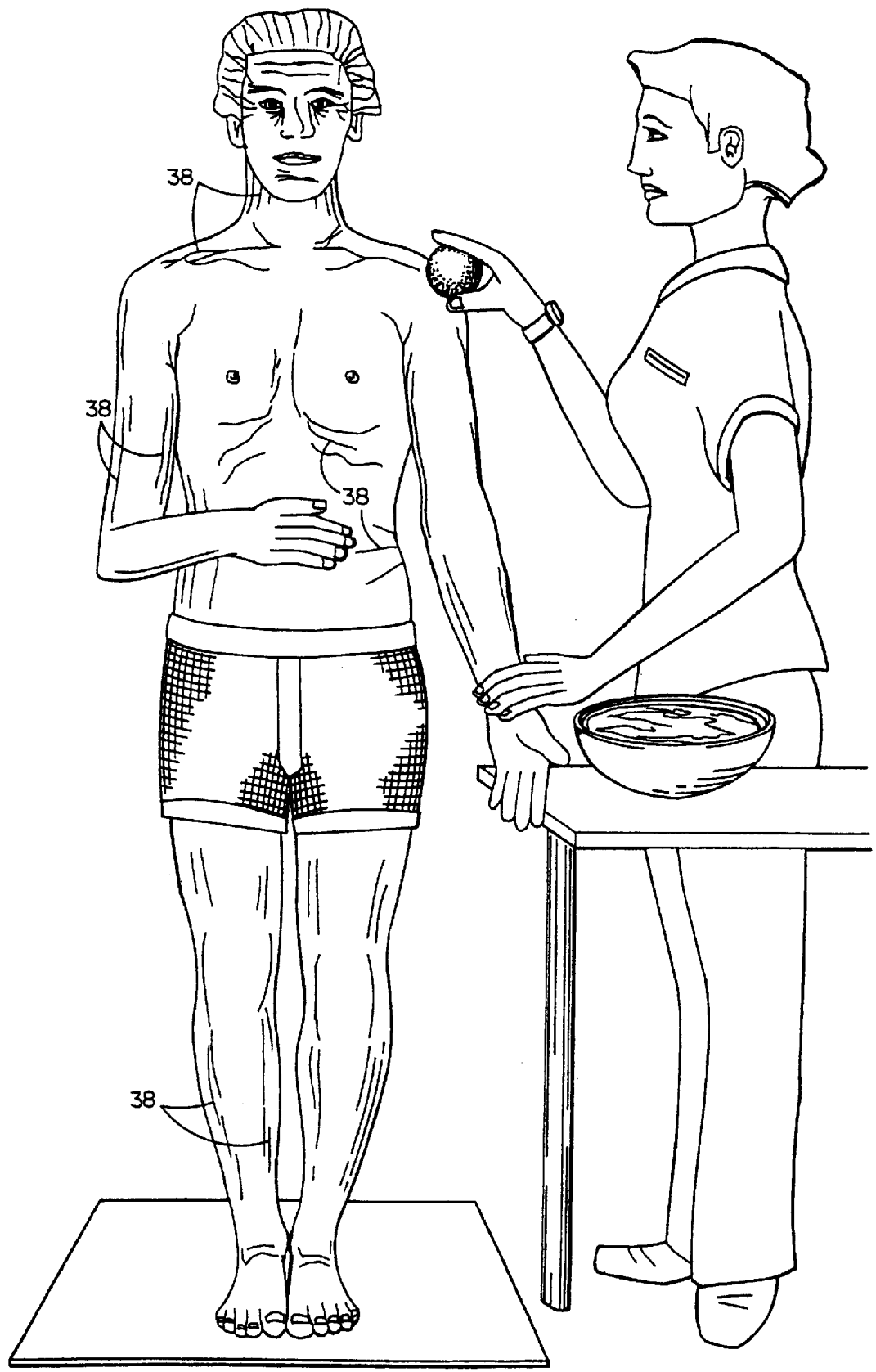
FIGS. 8a and 8b show a human recipient before and after being dabbed with the electrically charged substance to treat skin wrinkles.
Figure 8B:
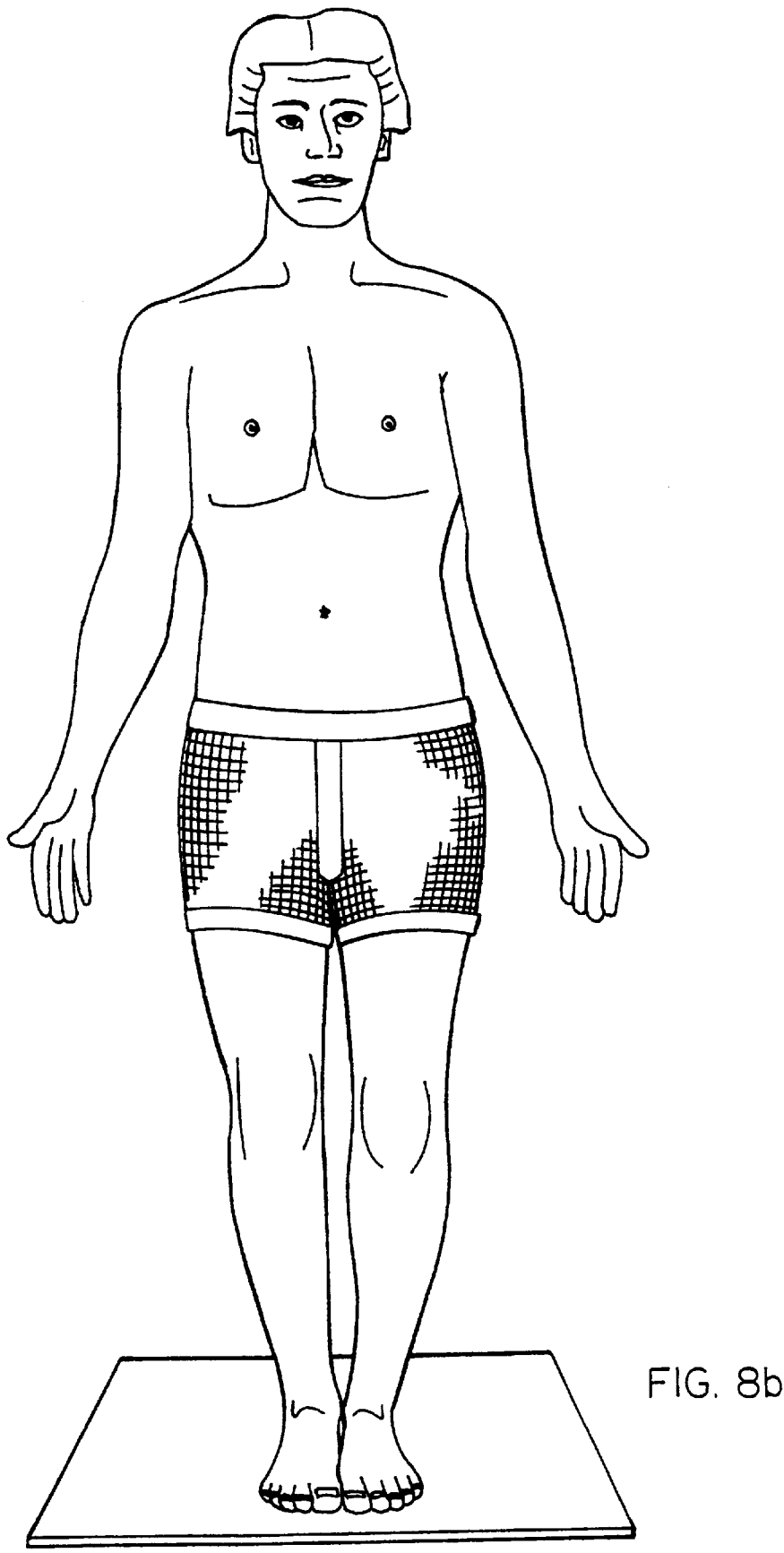
Figure 9:
FIG. 9 shows the electrically charged substance being dabbed onto an animal.
Figure 10:
FIG. 10 illustrates the electrically charged substance being administered to a recipient in the form of a gas.
Figure 12:
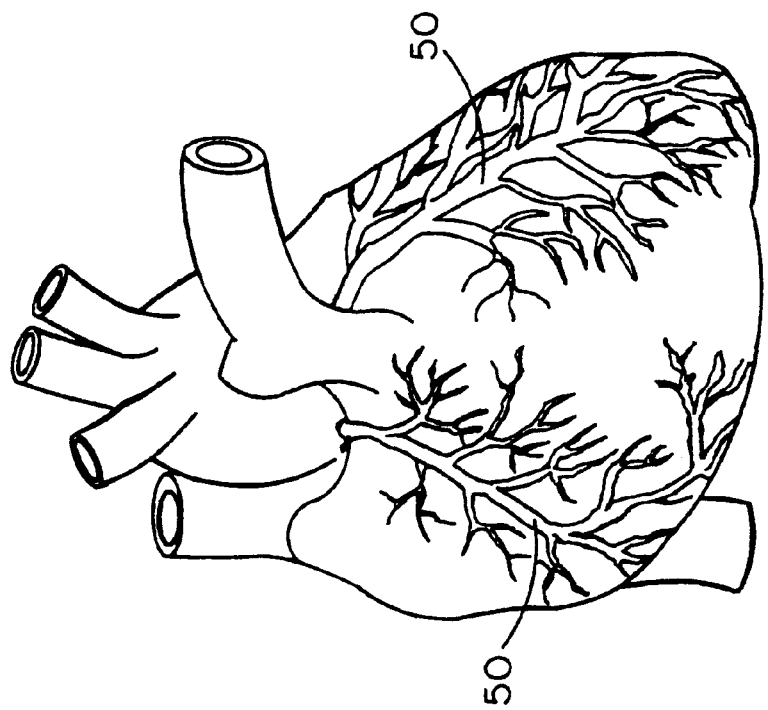
FIGS. 11 and 12 illustrate the dilation of capillaries and blood vessels after the administration of the electrically charged substance to a recipient.
Figure 11:
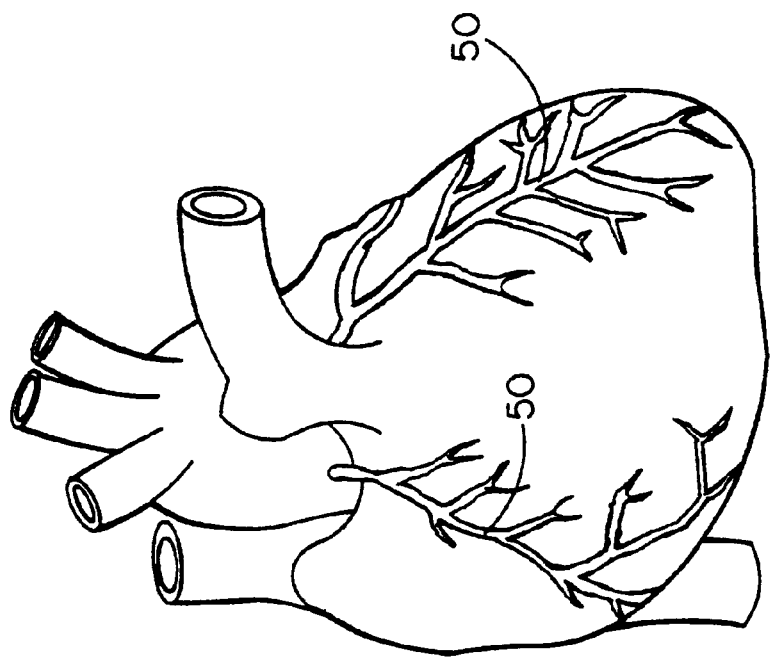

Referring now to FIG. 4, the method for forming an electrically activated substance of the present invention generally comprises providing distilled water 30, adding sodium chloride to the distilled water while monitoring current flow between the electrodes 32, applying alternating current to the electrodes 34, and, administering the electrically activated substance 36, preferably within four hours after the electrical activation thereof.

The electrically activated substance is only administered after first discontinuing the application of current thereto. In this manner, the electric current can be applied to an intermediate material, (i.e., the electrically activated substance), rather than directly to a person. Thus, as those skilled in the art will appreciate, a substantial amount of power may be applied to the electrically activated substance rather than directly to a person. Indeed, according to the preferred embodiment of the present invention, much more power, (e.g., approximately 100 watts), can applied to the electrically activated substance than could be tolerated by a human being.

The minimum amount of power applied to the substance during electrical activation thereof must be sufficient to overcome the activation decay rate of the substance. The more electrical power applied to the substance, the slower the rate at which the electrically activated substance's effectiveness decays. It has been found that the application of approximately 100 watts of electrical power to water results in an acceptable decay rate, as discussed in detail above.

Due to the relatively large amount of power used to electrically activate the water, a relatively high frequency is used. In this way, premature electrolysis (gassing) of the water is avoided. The high frequency also accelerates electron agitation in the medium. The pH balance of the medium is essentially unchanged.

Non-distilled or tap water or other bio-compatible compounds, including tissue, may be utilized instead of distilled water. It has been found that tap water is frequently suitable for use in the practice of the present invention. However, as those skilled in the art will appreciate, the types and amounts of impurities found in tap water vary considerably from one location to another. Thus, if an accurate analysis of the tap water to be utilized is not available, then the effectiveness thereof must be determined by trial and error.

Those skilled in the art will appreciate that various other electrolyte forming substances, other than sodium chloride are likewise suitable.

The application of alternating current 34 to the substance to be electrically charged preferably takes place for a duration of approximately 4 to 8 hours. When small gas bubbles appear on the electrodes, then the current has been applied for a sufficient length of time.

The electrically activated substance is created using the power levels, frequencies, current densities, and dosage quantities described herein, or parameters similar to those described herein. When the substance is produced in this manner, it takes on unique properties (possibly on an atomic level), which make it particularly well suited for the practice of the present invention.

It is understood that the exemplary electrically activated substance and method for making the same described herein and shown in the drawings represents only a presently preferred embodiment of the invention. Indeed, various modifications and additions may be made to such embodiment without departing from the spirit and scope of the invention. For example, various different sizes, shapes, and configurations of the container, the electrodes, and the source of alternating current are contemplated. Further, as those skilled in the art will appreciate, the use of water as the electrically activated substance is by way of example only, not by way of limitation. Indeed, it is also anticipated that gases, as well as liquids, may be electrically activated according to the present invention. Electrically activated gases may find particular application in the treatment of pulmonary disorders.

Thus, these and other modifications and additions may be obvious to those skilled in the art and may be implemented to adapt the present invention for use in a variety of different applications.

What is claimed is:

1. A method for cosmetically or medically treating a body area of a recipient in need of treatment, said method comprising the steps of:

placing an electrically conductive substance in a container such that said electrically conductive substance is separated from the body area of the recipient in need of treatment;

locating at least one pair of electrodes within the electrically conductive substance of said container and spacing said pair of electrodes from one another;

connecting an alternating current source to said at least one pair of electrodes and operating said alternating current source to generate an alternating current having a frequency that lies in a range of frequencies between 10 KHz and 1 MHz so that current flows through said electrically conductive substance and between said pair of electrodes for at least 10 minutes;

removing said alternating current flow through said electrically conductive substance after said at least 10 minutes; and applying said electrically conductive substance to the body area of the recipient within 4 days of removing the alternating current flow therethrough.

2. The method recited in claim 1, wherein said alternating current applied from said alternating current source to said electrically conductive substance has substantially no direct current bias.

3. The method recited in claim 1, wherein the electrically conductive substance is applied to the recipient for treating heart and circulatory conditions of the recipient.

4. The method recited in claim 1, including the additional step of topically applying the electrically conductive substance to the face of the recipient to treat facial wrinkles.

5. The method recited in claim 1, including the additional step of topically applying the electrically conductive substance to the skin of the recipient to treat a skin condition of the recipient.

6. The method recited in claim 1, including the additional steps of the recipient orally ingesting the electrically conductive substance.

7. The method recited in claim 1, including the additional step of the recipient orally ingesting the electrically conductive substance for treating skin wrinkles of the recipient.

8. The method recited in claim 1, including the additional step of the recipient receiving the electrically conductive substance internally for treating the organs of the recipient.

9. The method recited in claim 1, including the additional step of the recipient orally ingesting the electrically conductive substance for treating the organs of the recipient.

10. The method recited in claim 1, wherein the electrically conductive substance is applied to the body area of the recipient for treating scar tissue of the recipient.

11. The method recited in claim 1, wherein the electrically conductive substance is a liquid.

12. The method recited in claim 1, wherein the recipient is an animal.

13. The method recited in claim 1, including the additional step of operating said alternating current source to generate an alternating current having a frequency that lies in a range of frequencies between 50 KHz and 100 KHz.

14. A method for cosmetically or medically treating a body area of a recipient in need of treatment, said method comprising the steps of:

placing an electrically conductive substance in a container such that said electrically conductive substance is separated from the body area of the recipient in need of treatment;

locating at least one pair of electrodes within the electrically conductive substance of said container and spacing said pair of electrodes from one another;

connecting an alternating current source to said at least one pair of electrodes and operating said alternating current source to generate an alternating current having substantially no direct current bias and a frequency that lies in a range of frequencies between 10 KHz and 1 MHz so that current flows through said electrically conductive substance and between said pair of electrodes for at least 10 minutes;

removing said alternating current flow through said electrically conductive substance after said at least 10 minutes; and applying said electrically conductive substance to the body area of the recipient within 4 days of removing the alternating current flow therethrough.

15. The method recited in claim 14, wherein the electrically conductive substance is applied to the recipient for treating heart and circulatory conditions of the recipient.

16. The method recited in claim 14, including the additional step of topically applying the electrically conductive substance to the face of the recipient to treat facial wrinkles.

17. The method recited in claim 14, including the additional step of topically applying the electrically conductive substance to the skin of the recipient to treat a skin condition of the recipient.

18. The method recited in claim 14, including the additional step of orally ingesting the electrically conductive substance.

19. The method recited in claim 14, including the additional step of the recipient orally ingesting the electrically conductive substance for treating skin wrinkles of the recipient.

20. The method recited in claim 14, including the additional step of the recipient receiving the electrically conductive substance internally for treating the organs of the recipient.

21. The method recited in claim 14, including the additional step of the recipient orally ingesting the electrically conductive substance for treating the organs of the recipient.

22. The method recited in claim 14, wherein the electrically conductive substance is applied to the body area of the recipient for treating scar tissue of the recipient.

23. The method recited in claim 14, wherein the electrically conductive substance is a liquid.

24. The method recited in claim 14, wherein the recipient is an animal.

25. The method recited in claim 14, including the additional step of operating said alternating current source to generate an alternating current having a frequency that lies in a range of frequencies between 50 KHz and 100 KHz.

26. The method recited in claim 14, including the additional step of migrating direct current bias from said alternating current source to said electrically conductive substance by attaching a filter network between said current source and said pair of electrodes, said filter network having a capacitor connected in electrical series between said current source and one of said pair of electrodes and a resistor connected in electrical parallel with said capacitor and between said pair of electrodes.

27. The method as recited in claim 14, including the additional step of isolating said electrically conductive substance from direct current bias of said current source by connecting an isolation transformer between said alternating current source and said pair of electrodes.

28. A method for cosmetically or medically treating a body area of a recipient in need of treatment, said method comprising the steps of:
placing an electrically conductive fluid in a container such that said electrically conductive substance is separated from the body area of the recipient in need of treatment;
locating at least one pair of electrodes within the electrically conductive fluid of said container and spacing said pair of electrodes from one another;
connecting an alternating current source to said at least one pair of electrodes and operating said alternating current source to generate an alternating current having substantially no direct current bias and a frequency that lies in a range of frequencies between 10 KHz and 1 MHz, wherein the output power of said alternating current source is approximately 10 milliwatts per milliliter of said electrically conductive fluid in said container so that current flows through said electrically conductive fluid and between said pair of electrodes for at least 10 minutes;
removing said alternating current flow through said electrically conductive fluid after said at least 10 minutes; and
applying said electrically conductive fluid to the body area of the recipient within 4 days of removing the alternating current flow therethrough.

29. The method recited in claim 28, wherein the electrically conductive fluid is applied to the recipient for treating heart and circulatory conditions of the recipient.

30. The method recited in claim 28, including the additional step of topically applying the electrically conductive fluid to the face of the recipient to treat facial wrinkles.

31. The method recited in claim 28, including the additional step of topically applying the electrically conductive fluid to the skin of the recipient to treat a skin condition of the recipient.

32. The method recited in claim 28, including the additional step of the recipient orally ingesting the electrically conductive fluid.

33. The method recited in claim 28, including the additional step of the recipient orally ingesting the electrically conductive fluid for treating skin wrinkles of the recipient.

34. The method recited in claim 28, including the additional step of the recipient receiving the electrically conductive fluid internally for treating the organs of the recipient.

35. The method recited in claim 28, including the additional step of the recipient orally ingesting the electrically conductive fluid for treating the organs of the recipient.

36. The method recited in claim 28, wherein the electrically conductive fluid is applied to the body area of the recipient for treating scar tissue of the recipient.

37. The method recited in claim 28, wherein the recipient is an animal.

38. The method recited in claim 28, including the additional step of migrating direct current bias from said alternating current source to said electrically conductive fluid by attaching a filter network between said current source and said pair of electrodes, said filter network having a capacitor connected in electrical series between said current source and one of said pair of electrodes and a resistor connected in electrical parallel with said capacitor and between said pair of electrodes.

39. The method as recited in claim 28, including the additional step of isolating said electrically conductive fluid from direct current bias of said current source by connecting an isolation transformer between said current source and said pair of electrodes.

40. A method for cosmetically or medically treating a body area of a recipient in need of treatment, said method comprising the steps of:
placing an electrically conductive fluid in a container such that said electrically conductive substance is separated from the body area of the recipient in need of treatment;
locating at least one pair of electrodes within the electrically conductive fluid of said container and spacing said pair of electrodes from one another;
connecting an alternating current source to said at least one pair of electrodes and operating said alternating current source to generate an alternating current having substantially no direct current bias and a frequency that lies in a range of frequencies between 50 KHz and 100 KHz, wherein the output power of said alternating current source is approximately 10 milliwatts per milliliter of said electrically conductive fluid in said container so that current flows through said electrically conductive fluid and between said pair of electrodes for at least 10 minutes;
removing said alternating current flow through said electrically conductive fluid after said at least 10 minutes; and
applying said electrically conductive fluid to the body area of the recipient within 4 days of removing the alternating current flow therethrough.

41. A method for cosmetically or medically treating a body area of a recipient in need of treatment, said method comprising the steps of:
placing an electrically conductive fluid in a container such that said electrically conductive fluid is separated from the body area of the recipient in need of treatment;
locating at least one pair of electrodes within the electrically conductive fluid of said container and spacing said pair of electrodes from one another;
connecting an alternating current source to said at least one pair of electrodes and operating said alternating current source to generate an alternating current having substantially no direct current bias and a frequency that lies in a range of frequencies between 10 KHz and 1 MHz, wherein the output power of said alternating current source is approximately 10 milliwatts per milliliter of said electrically conductive fluid in said container so that current flows through said electrically conductive fluid and between said pair of electrodes for at least 10 minutes;
removing said alternating current flow through said electrically conductive fluid after said at least 10 minutes;

and applying said electrically conductive fluid to the body area of the recipient.

42. The method recited in claim 41, including the additional step of topically applying the electrically conductive fluid to the face of the recipient to treat facial wrinkles.

43. The method recited in claim 41, including the additional step of topically applying the electrically conductive fluid to the skin of the recipient to treat a skin condition of the recipient.

44. A method as recited in claim 20, wherein the electrolytic material is sodium chloride.

45. A method as recited in claim 34, wherein the electrolytic material is sodium chloride.

46. A method as recited in claim 19, wherein the current is monitored with an amp meter.

\* \* \* \* \*